United States Patent
Tian et al.

(10) Patent No.: US 6,958,426 B2
(45) Date of Patent: Oct. 25, 2005

(54) PROCESS FOR SEPARATING C5 CUTS OBTAINED FROM A PETROLEUM CRACKING PROCESS

(75) Inventors: Baoliang Tian, Beijing (CN); Puyang Li, Beijing (CN); Chunpeng Du, Beijing (CN); Hongfen Xu, Beijing (CN); Haiqiang Feng, Beijing (CN); Jingmin Hu, Beijing (CN); Jidong Gao, Beijing (CN); Ming Ma, Beijing (CN)

(73) Assignees: China Petroleum & Chemical Corporation, Beijing (CN); Beijing Research Institute of Chemical Industry Sinopec, Beijing (CN)

( * ) Notice: Subject to any disclaimer, the term of this patent is extended or adjusted under 35 U.S.C. 154(b) by 561 days.

(21) Appl. No.: 10/255,628

(22) Filed: Sep. 27, 2002

(65) Prior Publication Data

US 2003/0100809 A1 May 29, 2003

(30) Foreign Application Priority Data

Sep. 29, 2001 (CN) .......................................... 01136043
Oct. 12, 2001 (CN) .......................................... 01136383

(51) Int. Cl.⁷ .............................. C07C 4/06; C07C 7/09; C07C 7/10
(52) U.S. Cl. ....................... 585/329; 585/330; 585/809; 585/833
(58) Field of Search ................................. 585/329, 330, 585/809, 833

(56) References Cited

U.S. PATENT DOCUMENTS

| | | | |
|---|---|---|---|
| 2,971,036 A | * | 2/1961 | Donald ........................ 203/29 |
| 3,436,438 A | | 4/1969 | Takao et al. |
| 3,510,405 A | | 5/1970 | Takao et al. |

FOREIGN PATENT DOCUMENTS

| | | |
|---|---|---|
| CN | 1253130 | 5/2000 |
| CN | 96102485 | 9/2000 |
| JP | A 63 101338 | 5/1988 |

* cited by examiner

*Primary Examiner*—Thaun D Dang
(74) *Attorney, Agent, or Firm*—Birch, Stewart, Kolasch & Birch, LLP

(57) ABSTRACT

The present invention relates to a process for separating the isoprene, 1,3-pentadiene and dicyclopentadiene from a C5 cuts, comprising dimerization of the cyclopentadiene and selective catalytic hydrogenation. The second extractive rectification step can be omitted, because the alkynes are removed through selective catalytic hydrogenation prior to the extractive rectification. As a result, the solvent-recovering units can be simplified, and thus the process as a whole can be optimized. Correspondingly, the investment and energy consumption, the operation cost, and finally the production cost can be substantially reduced.

30 Claims, 2 Drawing Sheets

1. Light fraction removing rectification column;
2A. Thermal dimerization reactor;
2B. Heavy fraction pre-removing rectification column;
3. Hydrogenation reactor;
4. Extractive rectification column;
5. Stripping column;
6. Heavy fraction removing reaction rectification column;
7. C5-removing column;
8. 1,3-pentadiene refining column;
9. Dicyclopentadiene refining column 1. Light fraction removing rectification column;
2A. Thermal dimerization reactor;
2B. Heavy fraction pre-removing rectification column;
3. Hydrogenation reactor;
4. Extractive rectification column;
5. Stripping column;
6. Heavy fraction removing reaction rectification column;
7. C5-removing column;
8. 1,3-pentadiene refining column;
9. Dicyclopentadiene refining column

Figure 1

1. Light fraction removing rectification column;
2. Reaction rectification column;
3. Hydrogenation reactor;
4. Extractive rectification column;
5. Stripping column;
6. Heavy fraction removing rectification column;
7. C5-removing column;
8. 1,3-pentadiene refining column;
9. Dicyclopentadiene refining column

Figure 2

PROCESS FOR SEPARATING C5 CUTS OBTAINED FROM A PETROLEUM CRACKING PROCESS

TECHNICAL FIELD

This invention relates to a process for separating C5 cuts obtained from a petroleum cracking process, more particularly, to a process for separating C5 cuts obtained from a petroleum cracking process, comprising dimerization of the cyclopentadiene, selective hydrogenation to remove alkynes and one-step (that is, one-pass) extractive rectification, hereby separating isoprene, 1,3-pentadiene and dicyclopentadiene from C5 cuts.

BACKGROUND TECHNOLOGY

A large amount of C5 cuts is produced as by-products in the process for producing ethylene by petroleum cracking. The C5 cuts are rich in dienes such as isoprene, cyclopentadiene and 1,3-pentadiene. The dienes are reactive and thus are important raw materials in chemical industry. The amount of dienes in C5 cuts may vary depending upon the cracking raw materials, cracking degree and separation degree of the petroleum hydrocarbons, but the amount of total dienes in C5 cuts is in the range of from 40% to 60%. Therefore, it is of great significance to separate and utilize C5 cuts in order to improve the economic efficiency of ethylene units and fully utilize petroleum resources.

The C5 cuts from a cracking process consists of more than 20 components which have boiling points close to each other and can easily form azeotropes. Thus, a complicated process is needed to separate the valuable C5 dienes from the C5 cuts obtained from a cracking process. The C5 cuts contains a small amount of alkynes having 4 or 5 carbon atoms such as butyne-2, pentyne-1, pentyne-2 and isopropenyl acetylene (hereinafter referred to as valylene). The amount of the total alkynes is about 0.1–2 wt %. Due to their chemical reactivity, the alkynes are major impurities harmful to the reaction and polymerization of C5 diene products. Therefore, it is an important step in the process for separating the C5 cuts to efficiently remove the alkynes.

In order to produce C5 dienes having a high purity, an extractive rectification process is widely used in the art. The advantage of the process is that the amount of the total alkynes in the isoprene product can be reduced to 50 ppm or less while removing a minor amount of cyclopentadiene. The disadvantage of the process is that the energy consumption is high and the alkynes will accumulate in certain units during the separation, thereby resulting in a risk for operation. The conventional selective solvents include dimethylformamide (DMF) and acetonitrile as are used in, for example, JP63101338, U.S. Pat. No. 3,510,405 and U.S. Pat. No. 3,436,438.

U.S. Pat. No. 3,510,405 (Japanese Geon, Co. Ltd., Tokyo, Japan) discloses a process for separating the isoprene having a high purity from C5 cuts, comprising:

subjecting C5 cuts obtained by a hydrocarbon steam cracking or other pyrolysis cracking to a thermal dimerization and separating the resulting dicyclopentadiene;

conducting the first extractive rectification in the presence of a polymerization inhibitor and DMF as a solvent that was recovered in a stripping column for recycling;

rectifying the materials in a heavy fraction removing rectification column to separate heavy fractions comprising cyclopentadiene and 1,3-pentadiene;

conducting the second extractive rectification in the presence of a polymerization inhibitor and DMF as a solvent that is recovered in a stripping column for recycling; and rectifying the materials in a light fraction removing column and obtaining an isoprene product of high purity at the bottom.

CN1253130A discloses a reaction rectification process wherein C5 cuts as a raw material is subjected to a reaction rectification without dimerization. The disadvantage of the process is that a large amount of cyclopentadiene is produced at the top of the column and it is difficult to operate the column.

CN1056823A discloses a process for removing most of the alkynes contained in C5 cuts by rectification prior to an extractive separation. An advantage of the process is that the risk of the explosion of the alkynes can be avoided during the course of the separation of C5 cuts due to the removal of most of the alkynes and thus ensures a safe production. Meantime, the load for the subsequent steps and the amount of solvent for the extraction can be reduced and thus the processing ability of the process as a whole can be improved. However, the C5 cuts at the bottom still contain more than 200 ppm of alkynes. Therefore, two-step extractive rectification is necessary to obtain isoprene suitable for polymerization.

Generally, a separation process of C5 cuts comprises two-step extractive rectification and two-step conventional rectification in the prior art, in order to obtain isoprene suitable for polymerization. Furthermore, it is necessary for the solvent to be recovered and refined in certain solvent-recovery unit. Therefore, the energy consumption, investment and operation cost is high due to the complicated procedure. Specifically, there exist following problems: 1) The number of steps is large, and the investment is high. Accordingly, both the operation cost and energy consumption increase. 2) The equipment may be fouled with black dregs and a large amount of tarry materials build up in the solvent-recovering unit, which are difficult to be cleaned; 3) A large amount of the solvent, about 20 kg solvent/ton product is used and thus the production cost is increased.

DISCLOSURE OF THE INVENTION

The present inventor proposed a process for separating C5 cuts by a combination of a particular cyclopentadiene dimerization and a selective hydrogenation to remove any alkynes in order to overcome the above-mentioned problems in the separation of C5 cuts in the prior art. In such a process, the chemical products of high purity such as isoprene, 1,3-pentadiene and dicyclopentadiene can be separated out by extractive rectification only one time. In addition, alkynes such as valylene, butyne-2 and pentayne-1 in the C5 cuts are converted into alkenes such as isoprene, butene-2 and pentene-1 in the selective hydrogenation step so that the content of residual alkynes is less than 20 ppm by weight.

Figure 1:
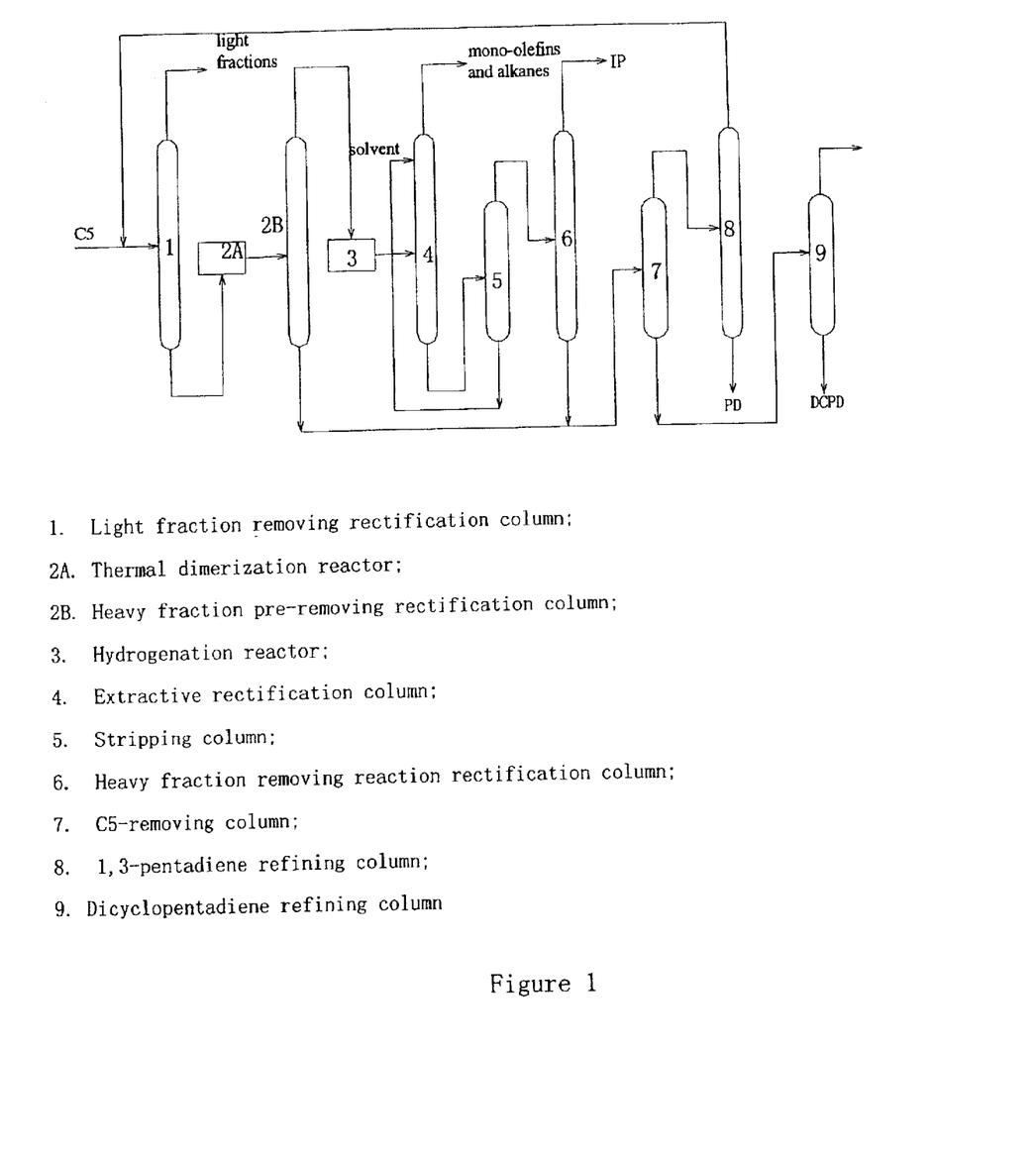
FIG. 1 shows a flow diagram of the separation process for C5 cuts according to the present invention, comprising the thermal dimerization and the heavy fraction pre-removing rectification
Figure 2:
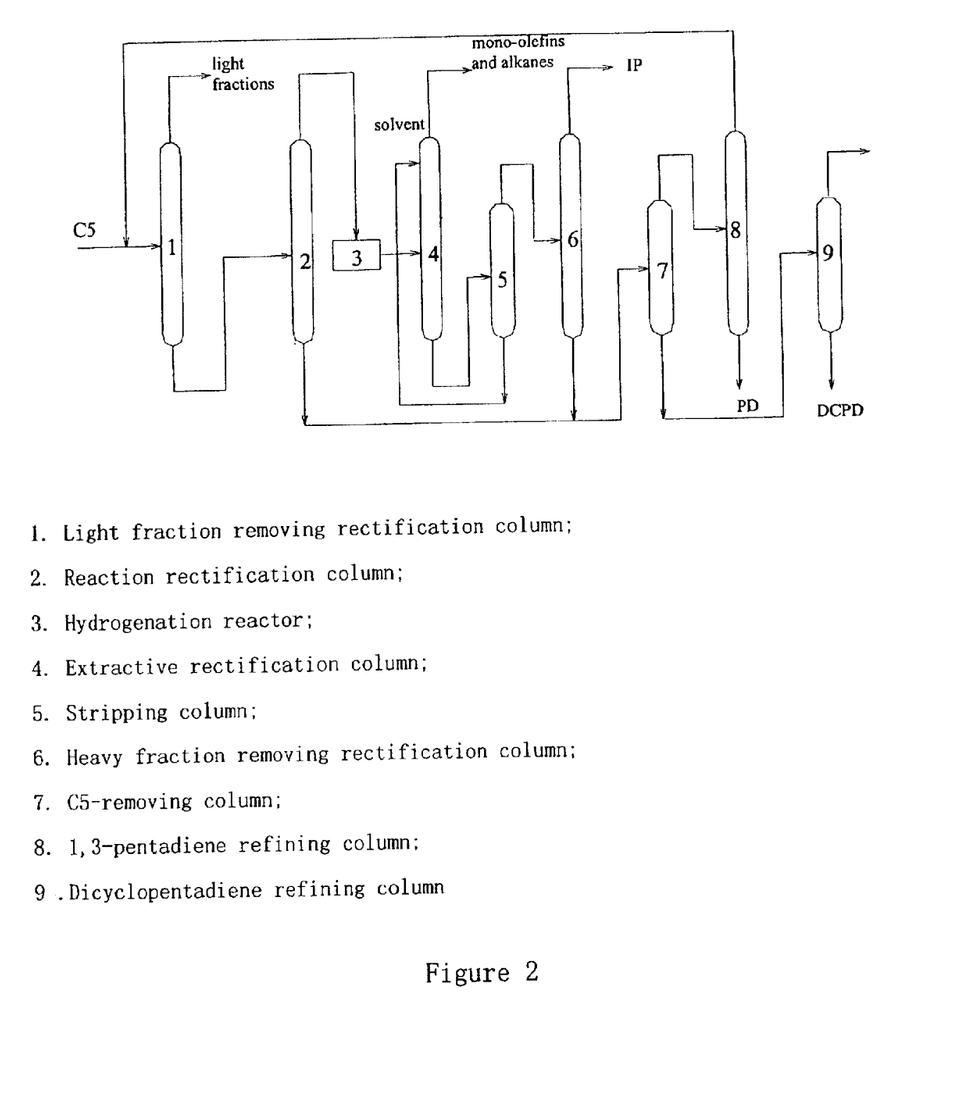
FIG. 2 shows a flow diagram of the separation process for C5 cuts according to the present invention, comprising the reaction rectification in place of the thermal dimerization and the heavy fraction pre-removing rectification.

The process for separating C5 cuts according to the present invention comprises:

1) a light fraction-removing step, wherein C5 cuts obtained from petroleum cracking unit as a raw material is fed into the middle section of a light fraction-removing rectification column 1 for rectification, with the light materials having 4 or less carbon atoms being obtained at the top of the column and C5 material being obtained at the bottom of the column;

2) a heavy fraction pre-removing step, wherein the bottoms from step 1) are fed into a thermal dimerization reactor 2A where a thermal dimerization is carried out and cyclopentadiene in C5 cuts is dimerized to form dicyclopentadiene. Preferably, the reaction is conducted at a temperature of 60–150° C. and a pressure of 1.0–1.5 MPa (absolute pressure, hereinafter the same). Then the materials are fed into a heavy fraction pre-removing rectification column 2B, with dicyclopentadiene, 1,3-pentadiene and other heavy materials being obtained at the bottom and isoprene, mono-olefins, alkanes, alkynes and cyclopentadiene etc. being obtained at the top;

alternatively, the bottoms from step 1) are fed into a heavy fraction pre-removing reaction rectification column 2 where dimerization reaction and rectification separation are carried out simultaneously. The process is preferably conducted under a condition of a plate number of 50–120, a bottom temperature of 70–110° C., a top temperature of 35–70° C., a reflux ratio of 20–80 and a pressure of 0.01–0.20 MPa so that cyclopentadiene therein is dimerized to form dicyclopentadiene, with dicyclopentadiene, 1,3-pentadiene and other heavy materials being obtained at the bottom and isoprene, mono-olefins, alkanes, alkynes, cyclopentadiene and 1,3-pentadiene being obtained at the top. The content of cyclopentadiene at the top is less than 2%. The overhead stream is fed into a hydrogenation reactor 3, and optionally the bottoms are fed into C5-removing column 7;

3) a catalytic hydrogenation step, wherein the overhead stream from step 2) are fed into a hydrogenation reactor 3 where a selective hydrogenation is carried out in order to remove alkynes such as valylene and butyne-2. A selective hydrogenation catalyst for alkynes is packed in the reactor 3. The reactor 3 is operated under a condition of a temperature of preferably 20–80° C., a pressure of preferably 0.3–4.0 MPa, a liquid space velocity of preferably 2–15 $m^3/m^3 \cdot hr$ and a ratio of preferably 1–30 mole hydrogen/mole alkyne;

4) an extractive rectification step, wherein the materials from step 3) are fed into the middle section of an extractive rectification column 4. A solvent and a polymerization inhibitor are added to the top of the column, and an extractive rectification is carried out in the presence of the solvent and the polymerization inhibitor. The conditions are preferably as follows: a plate number of 70–150, an column pressure of 0.01–0.3 MPa, a bottom temperature of 100–150° C., a top temperature of 40–80° C., a reflux ratio of 4–15 and a solvent ratio of 3–12. Wherein said solvent is selected from the group consisting of dimethylformamide, dimethylacetamide, acetonitrile, N-methyl pyrrolidone and the mixtures thereof. And, wherein the polymerization inhibitor is selected from the group consisting of sodium nitrite and ethanolamine composite, o-nitrophenol, nitrobenzene and furfural. Preferably, wherein the polymerization inhibitor is sodium nitrite and ethanolamine composite, and the concentration of sodium nitrite in C5 materials is 200–1500 ppm and the concentration of ethanolamine in C5 materials is 100–700 ppm. Mono-olefins and alkanes are obtained at the top and the isoprene-rich and solvent-based materials of C5 dienes are obtained at the bottom;

5) a stripping step, wherein the solvent-based materials at the bottom from step 4) are fed into a stripping column 5 operating under a condition of a plate number of 20–60, a top temperature of 30–55° C., a bottom temperature of 120–200° C., a top pressure of 0.05–0.3 MPa, a bottom pressure of 0.08–0.5 MPa and a reflux ratio of 1–5. The recovered solvent at the bottom can be returned to the extractive rectification column 4 for recycling; and 6) a heavy fraction-removing step, wherein the materials obtained at the top of the stripping column 5 are fed into a heavy fraction-removing reaction rectification column 6 where a rectification is carried out, with dicyclopentadiene, 1,3-pentadiene and other heavy materials being obtained at the bottom and isoprene product of a polymerization grade being obtained at the top; and optionally, 7) a C5-removing step, wherein the bottoms of the heavy fraction pre-removing rectification column 2B or the heavy fraction pre-removing reaction rectification column 2 are fed into a C5-removing column 7 together with the bottoms of a heavy fraction-removing reaction rectification column 6. Preferably, the plate number is 15–50, the top temperature is 40–55° C., the bottom temperature is 95–120° C., the top pressure is 0.01–0.03 MPa, the bottom temperature is 0.02–0.07 MPa and the reflux ratio is 0.5–3. C5 hydrocarbons are obtained at the top of the C5-removing column; and 8) a step of refining 1,3-pentadiene and dicyclopentadiene, wherein C5 hydrocarbons at the top of the C5-removing column 7 are fed into a 1,3-pentadiene refining column 8 for refining. The operation conditions are preferably as follows: a plate number of 70–120, a top temperature of 40–60° C., a bottom temperature of 50–70° C., a top pressure of 0.02–0.1 MPa, a bottom pressure of 0.07–0.15 MPa and a reflux ratio of 30–70. 1,3-pentadiene product is obtained at the bottom with a purity of above 65%. The overhead stream is returned to the C5-cut line as raw material. The bottoms of C5-removing column 7 are fed to the middle section of a dicyclopentadiene refining column 9 with a plate number of 70–160, a top temperature of 20–50° C., a bottom temperature of 90–120° C., an column pressure of −0.05~−0.12 MPa and a reflux ratio of 1–5. The dicyclopentadiene product is obtained at the bottom with a purity of above 80%.

By the wording "isoprene product of a polymerization grade" throughout the whole text of the present application is meant an isoprene product which meets following requirements: isoprene, $\geq 99.3\%$; alkanes and mono-olefins, $\leq 0.7\%$; isoprene dimer, $\leq 0.1\%$; total alkynes, $\leq 50$ ppm; 1,3-pentadiene, $\leq 80$ ppm; cyclopentadiene, $\leq 1$ ppm; sulfur, $\leq 5$ ppm; and carbonyl compounds, $\leq 10$ ppm.

In the light fraction-removing column 1, the inlet temperature of C5 cuts is preferably 30–75° C., the bottom temperature is 75–96° C., the top temperature is 40–60° C., the top pressure is 0.1–0.3 MPa, the bottom pressure is 0.2–0.4 MPa, the plate number is 50–100 and the reflux ratio is 15–32.

Preferably, the heavy fraction pre-removing rectification column 2B is also a reaction rectification column, where the unreacted cyclopentadiene is further reacted to form dicyclopentadiene, with 1,3-pentadiene, dicyclopentadiene and other heavy materials being obtained at the bottom, and isoprene, mono-olefins, alkanes, alkynes and cyclopentadiene etc. being obtained at the top, so that the content of cyclopentadiene in the overhead stream is less than 2%. Preferably, the plate number is 30–80, the bottom temperature is 50–110° C., the top temperature is 35–70° C., the reflux ratio is 0.5–25 and the operation pressure is 0.01–0.20 MPa.

Cyclopentadiene is reacted to form dicyclopentadiene in the heavy fraction pre-removing reaction rectification column 2, with 1,3-pentadiene, dicyclopentadiene and other heavy materials being obtained at the bottom, and isoprene, mono-olefins, alkanes, alkynes and cyclopentadiene etc. being obtained at the top, so that the content of cyclopentadiene in the overhead stream is less than 2%. Preferably, the plate number is 50–120, the bottom temperature is 70–110° C., the top temperature is 35–70° C., the reflux ratio is 20–80 and the operation pressure is 0.01–0.20 Mpa.

As a selective hydrogenation catalyst for alkynes packed in the catalytic hydrogenation reactor 3, a supported catalyst can be employed, comprising a notable metal as an active component on a support such as aluminum oxide. The support is employed at an amount of more than 50%, preferably more than 90%, based on the total weight of the catalyst. Preferably, aluminum oxide is employed as the support. The catalyst additionally comprises:

(1) at least one metal selected from the IB group of the Elemental Periodic Table at an amount of 0.1–10%, preferably 1–8%, more preferably 2–6%, wherein Cu accounts for more than 90%, preferably more than 95%, particularly preferably 99%, of the total weight of the metals of the group, the balance being other metals of the group;

(2) at least one metal selected from the VIII group of the Elemental Periodic Table at an amount of 0.008–1%, preferably 0.01–0.2%, more preferably 0.01–0.1%;

(3) at least one alkali metal at an amount of 0.01–0.5%, preferably 0.1–2%, more preferably 0.2–1%.

In the Elemental Periodic Table, the IB group consists of Cu, Ag and Au and the VIII group consists of Fe, Co, Ni, Rh, Ru, Pd, Os, Ir and Pt. As a metal in IB group, Cu and Ag are preferably employed together as double metals. As a metal in VIII group, Ni, Pd, Pt and/or Rh can be preferably employed. In particular, Pd is employed as a single metal of the group. The alkali metals comprise Li, Na and K etc. Preferably K is employed as a single alkali metal. The active components of the catalyst preferably comprise Cu, Ag, Pd, and K.

If necessary or needed, the active components of the catalyst can comprise elements other than elements in VIII group, IB group of the Elemental Periodic Table and alkali metals. Specifically, the catalyst can further comprise additional additives and/or activators, such as zinc or fluorides. Generally, the content of the activators added is from several ppms to several thousand ppms.

The support of the catalyst according to the present invention comprises essentially aluminum oxide and can additionally comprise certain additives such as silica, titanium oxide, zirconium oxide, zinc oxide, magnesium oxide, sodium oxide and calcium oxide. Generally, the content of the oxides except aluminum oxide is less than 50% by weight, preferably less than 10% by weight, and particularly preferably, the support consists of aluminum oxide. As aluminum oxide, conventional aluminum oxide or conventional partly hydrated aluminum oxide can be employed, such as a $\alpha$-, $\beta$-, $\gamma$-, $\delta$-, $\theta$- or $\chi$—$Al_2O_3$, boehmite, pseudo-boehmite or mixtures thereof.

The support employed in the catalyst according to the present invention can be in the form of pellets, spheres, stripes, rings, or gears, preferably spheres. The specific surface area of the support as measured by the BET (Brunauer-Emmett-Teller) method is generally 200–350 $m^2/g$, preferably 220–320 $m^2/g$. The pore volume of the support is generally 0.1–1.0 ml/g, preferably 0.2–0.8 ml/g. The average pore diameter of the support is generally 4–40 nm, preferably 6–30 nm, particularly preferably at most 20 nm. Preferably, the support according to the present invention is calcined at a temperature of 300–800° C. for 2–10 hours prior to impregnation. The specific surface area as measured by the BET method is determined by tester SORPTOMATIC, Model 1990, available from FISSONS Corp. The experimental conditions are as follows:

(1) pretreatment:
 a temperature of 120–350° C.;
 a vacuum of less than 1 Pa for a period of 4–6 hours
(2) measurement of the specific surface area:
The specific surface area of a sample adsorbing nitrogen at a temperature of liquid nitrogen is determined by a static multi-point BET method.

In accordance with the present invention, the catalyst is prepared by impregnating the support at one time or batch-wise with a nitric acid solution of a salt of IB group metal, with a nitric acid solution of a salt of VIII group metal, and with an aqueous solution of an alkali metal compound in this order; drying the impregnated support at a temperature of 50–200° C. to remove water after each step of impregnation; and optionally calcining the dried support at a temperature of 250–650° C.

In accordance with the present invention, the support is impregnated respectively with solutions of metals in each group. Firstly, the support is impregnated with a nitric acid solution of a salt of IB group metal and then with a nitric acid solution of a salt of VIII group metal. The salts of IB group metal and VIII group metal are soluble salts such as nitrate, chloride, acetate, sulfate and the like, with the proviso that no precipitate is formed. Nitrate is preferred. Nitric acid is employed at such an amount that a clear solution is formed. The pH value of the solution is 0.1–3, preferably 0.2–2.

Finally, the support is impregnated with an aqueous solution of an alkali metal compound, preferably an aqueous solution of hydroxide, halide or nitrate, particularly preferably an aqueous solution of hydroxide. The volume of the solution employed for impregnation is not more than the largest absorption volume of the support in each step. The concentration of the compound in the solution is determined as follows: the concentration is such that the deposited components reach the desired content in the catalyst after the completion of the impregnation and after the conversion of the impregnated support into the catalyst product.

After each step of impregnation, the impregnated support is dried at a temperature of 50–200° C., preferably 60–190° C., particularly preferably 70–180° C. Drying is continued until the water contained in the impregnated support is essentially completely removed, which generally needs several hours. The period of drying depends on the drying temperature employed. The higher the temperature is, the shorter the period is. Generally, the period of drying is in a range of from 1 hour to 20 hours.

In principle, the dried catalyst can be used directly. The deposited metal compound can be directly reduced to the metal in the presence of hydrogen gas or a hydrogen-containing gas in a hydrogenation reactor. However, the catalyst is preferably calcined after being dried in order that the compound employed is converted into deposited components or precursors of the components. In the case of impregnation with a metal compound, the metal compound upon calcination essentially breaks down into metals and/or metal oxides remaining in the catalyst. The calcination temperature is generally 200–650° C., preferably 300–550° C., particularly preferably 380–520° C. The period of the calcination is generally 0.5–20 hours. The calcination is preferably carried out at most 15 hours, particularly preferably at most 10 hours. The calcination is conducted in a common furnace, such as a spinning tube furnace, a channel furnace or a muffle furnace. Calcination can be carried out immediately after drying and thus an immediate cooling of the impregnated and dried support is unnecessary.

If necessary or needed, the metal oxide is reduced to metal during or prior to the use of the calcined catalyst in the hydrogenation reactor. That is, both oxides of VIII group metal and those of IB group metal are converted into the metals, which naturally takes place in the case of hydrogenation or is carried out by conventional methods.

The process of selective hydrogenation for C5 cuts to remove alkynes is generally carried out in a gas/liquid phase. C5 cuts are in a liquid form and hydrogen is in a gaseous form and/or is dissolved in a liquid phase. The reaction conditions, such as the pressure, temperature, flow rate and hydrogen amount, are so designed that alkynes are removed. Based on the volume of catalyst, the liquid space velocity of C5 cuts is 2–15 $m^3/m^3 \cdot h$, the temperature is 20–80° C. and the pressure is 0.3–4.0 MPa. The hydrogen is added at such an amount that the loss of C5 dienes is minimum while removing alkynes. The amount of hydrogen added is at least 1 mole, preferably at least 2 mole, and at most 30 mole, preferably at most 20 mole, per mole alkyne.

The catalyst according to the present invention exhibits good catalytic performance. Specifically, the catalyst provides a high activity, good selectivity and a long lifetime during the selective hydrogenation of alkynes in C5 cuts.

By means of the selective hydrogenation of C5 cuts to remove alkynes, the alkyne content in the materials can be reduced to less than 20 ppm and the loss of the valuable dienes is less than 2%. Including such step, the process for separating C5 cuts can be simplified and the investment, energy consumption and the loss of the solvent can be reduced.

Preferably, the heavy fraction-removing reaction rectification column 6 is a reaction rectification column where the unreacted cyclopentadiene is dimerized to form dicyclopentadiene, which is easy to be separated away from isoprene. Preferably, the plate number is 100–200, the top temperature is 40–55° C., the bottom temperature is 60–90° C., the top pressure is 0.01–0.15 MPa, the bottom pressure is 0.05–0.25 MPa and the reflux ratio is 15–60.

Optionally, in the steps 7)–8) of the process, the bottoms from the heavy fraction pre-removing rectification column 2B or the heavy fraction pre-removing reaction rectification column 2 and the heavy fraction-removing reaction rectification column 6 are fed into columns 7, 8 and 9 for rectification. As a result, other C5 hydrocarbon components and C6 hydrocarbon components are removed, while 1,3-pentadiene and dicyclopentadiene products having a high purity are respectively obtained.

In the process according to the present invention, when both the heavy fraction pre-removing rectification column 2B and the heavy fraction-removing reaction rectification column 6 are reaction rectification columns, the materials out of the top of the heavy fraction pre-removing rectification column 2B can be directly fed into the extractive rectification column 4. Isoprene(chemically pure) can be obtained at the top of the heavy fraction-removing reaction rectification column 6. That is to say, the purity of the isoprene product obtained is above 98%.

The process according to the present invention has following advantages over the prior art.

(1) The process is simplified and the second extractive rectification unit can be omitted. As a result, the loss of the solvent is reduced and the solvent-recovering unit can be simplified;
(2) The fouling of the equipment with black dregs resulting from the hydrolyzing of the solvent can be avoided;
(3) The construction expenses, operation costs and energy consumption are all reduced. Generally, the investment and production cost are reduced by at least 15–20% as compared with the prior art.

According to one embodiment of the present invention, as mentioned above, a reaction rectification step can replace the thermal dimerization and the heavy fraction pre-removing rectification so that the thermal dimerization reactor can be omitted. During the course of thermal dimerization, due to the desired high operation temperature, there exist dimers and copolymers produced from the homo-dimerization and co-dimerization of isoprene, 1,3-pentadiene and cyclopentadiene, which have a boiling point close to that of dicyclopentadiene and thus are difficult to be separated away from dicyclopentadiene. Therefore, the purity of dicyclopentadiene products and thereby the yield of C5 dienes is adversely affected. The reaction rectification step in place of the thermal dimerization step will efficiently inhibit the dimerizations other than the cyclopentadiene dimerization, reduce the formation of by-products and thus increase the purity of cyclopentadiene products. In this way, the application value is increased. Meantime, the process is simplified, the equipment investment and the energy consumption in the production are further reduced.

Unless otherwise indicated, all ratios or contents used in the present application are by weight.

EXAMPLES

Examples 1–9 illustrate the process for producing the hydrogenation catalysts according to the present invention and comparative catalysts. Example 10 illustrates the results of selective hydrogenation using the hydrogenation catalysts according to the present invention and the comparative catalysts. Example 11 illustrates a process for separating C5 cuts according to the present invention, comprising thermal dimerization and heavy fraction pre-removing rectification. Example 12 illustrates a process for separating C5 cuts according to the present invention, comprising reaction rectification in place of thermal dimerization and heavy fraction pre-removing rectification.

Example 1

Preparation of Catalyst-1

30 g of aluminum oxide as the support (the specific surface area measured by the BET method is 287 $m^2/g$) was impregnated with a mixture of 0.18% (by weight of copper) aqueous copper nitrate solution and a 0.2% (by weight of silver) aqueous silver nitrate solution, which mixture had been previously regulated to a volume of 22.5 ml and a pH of 1.0 using nitric acid and water, dried at 120° C. for 4 hours, calcined at 500° C. for 4 hours, and then cooled down to room temperature. Then the resulting support was impregnated with a 0.2% (by weight of palladium) aqueous palladium nitrate solution (also regulated to a volume of 22.5 ml and a pH of 1.0 using nitric acid and water), dried and calcined as above, and cooled to the room temperature. The resulting support was impregnated with a 2% (by weight of potassium) aqueous potassium hydroxide solution, dried and calcined as above. The above solutions were used at such an amount that the obtained catalyst contained 3 wt % of copper, 0.04 wt % of silver, 0.04 wt % of palladium and 0.3 wt % of potassium.

The resulting catalyst was referred to as Cat. 1.

Example 2

Preparation of Catalyst-2

This example was carried out as in Example 1, except that the solutions were used at such an amount that the resulting catalyst contained 6% of copper, 0.03% of silver, 0.06% of palladium and 0.6% of potassium.

The resulting catalyst was referred to as Cat.2.

Example 3

Preparation of Catalyst-3

This example was carried out as in Example 1, except that the solutions were used at such an amount that the resulting catalyst contained 3% of copper, 0.03% of silver, 0.03% of palladium and 0.3% of potassium.

The resulting catalyst was referred to as Cat.3.

Example 4

Preparation of Catalyst C-1

This example was carried out as in Example 1, except that the support was firstly impregnated with the potassium solution, then with the copper and silver solutions, and finally with the palladium solution.

The obtained catalyst was referred to as C-1.

Example 5

Preparation of Catalyst C-2

This example was carried out as in Example 1, except that the support was firstly impregnated with the palladium solution, then with the copper and silver solutions, and finally with the potassium solution.

The obtained catalyst was referred to as C-2.

Example 6

Preparation of Catalyst C-3

This example was carried out as in Example 1, except that the solutions were used at such an amount that the resulting catalyst contained 10% of copper, 0.3% of silver, 0.3% of palladium and 3% of potassium.

The obtained catalyst was referred to as C-3.

Example 7

Preparation of Catalyst C-4

This example was carried out as in Example 1, except that the solutions were used at such an amount that the resulting catalyst contained 0.8% of copper, 0.1% of silver, 0.005% of palladium and 0.05% of potassium.

The obtained catalyst was referred to as C-4.

Example 8

Preparation of Catalyst C-5

This example was carried out as in Example 1, except that aluminum oxide with a BET specific surface area of 366 $m^2/g$ was employed as the support.

The obtained catalyst was referred to as C-5.

Example 9

Preparation of Catalyst C-6

This example was carried out as in Example 1, except that aluminum oxide with a BET specific surface area of 180 $m^2/g$ was employed as the support.

The obtained catalyst was referred to as C-6.

Example 10

Selective Hydrogenation

In order to evaluate the catalytic performances of catalysts Cat.1, Cat.2, Cat.3 according to the present invention and comparative catalysts C-1, C-2, C-3, C-4, C-5 and C-6, alkynes contained in an isoprene stream were selectively hydrogenated in an experimental apparatus equipped with a fixed-bed reactor. An isoprene feed having a purity of 99.8 wt % containing 950 ppm of alkynes (butyne-2 and valylene), was mixed with hydrogen and then passed through the catalyst bed at a pressure of 0.8 MPa. The molar ratio of hydrogen to alkynes added into C5 cuts is 11. The reaction temperature is 40° C., the liquid space velocity of the feed is 8 $m^3/m^3 \cdot h$. The selectively hydrogenated material was analyzed by gas chromatograph.

The lifetime, activity and selectivity of catalysts were shown in Table 1.

TABLE 1

| | | | | Evaluation of catalysts | | | | |
|---|---|---|---|---|---|---|---|---|
| | | amounts of supported | BET specific surface area of | | initial period of reaction | | period of continuous | period end of reaction |
| catalyst | | components Cu/Ag/Pd/K (%) | support ($m^2/g$) | impregnation order | alkynes (ppm) | loss of IP (%) | run (hr) | alkynes (ppm) | loss of IP (%) |
| 1 | | 3/0.04/0.04/0.3 | 287 | Cu—Ag/Pd/K | 38 | 1.4 | 600 | 39 | 1.2 |
| 2 | | 6/0.03/0.06/0.6 | 287 | Cu—Ag/Pd/K | 29 | 1.5 | 600 | 30 | 1.5 |
| 3 | | 3/0.03/0.03/0.3 | 287 | Cu—Ag/Pd/K | 44 | 1.3 | 600 | 44 | 1.3 |

TABLE 1-continued

Evaluation of catalysts

| catalyst | amounts of supported components Cu/Ag/Pd/K (%) | BET specific surface area of support (m²/g) | impregnation order | initial period of reaction | | period of continuous run (hr) | period end of reaction | |
|---|---|---|---|---|---|---|---|---|
| | | | | alkynes (ppm) | loss of IP (%) | | alkynes (ppm) | loss of IP (%) |
| C-1 | 3/0.04/0.04/0.3 | 287 | K/Cu—Ag/Pd | 33 | 1.7 | 41 | 94 | 1.5 |
| C-2 | 3/0.04/0.04/0.3 | 287 | Pd/Cu—Ag/K | 75 | 1.5 | 64 | 101 | 1.9 |
| C-3 | 10/0.3/0.3/3 | 287 | Cu—Ag/Pd/K | 8 | 3.4 | 30 | 42 | 2.8 |
| C-4 | 0.8/0.1/0.005/0.05 | 287 | Cu—Ag/Pd/K | 87 | 1.9 | 28 | 121 | 1.4 |
| C-5 | 3/0.04/0.04/0.3 | 366 | Cu—Ag/Pd/K | 30 | 1.8 | 72 | 64 | 1.5 |
| C-6 | 3/0.04/0.04/0.3 | 180 | Cu—Ag/Pd/K | 69 | 1.1 | 72 | 73 | 1.1 |

Note: The expression "Cu—Ag/Pd/K" means that the aluminum oxide support was firstly impregnated with a mixture of copper and silver solutions, then with the palladium solution, and finally with the potassium solution. Other expressions have the similar meanings.

It can be seen from Table 1 that the catalysts Cat.1–Cat.3 according to the present invention showed no substantial changes in their catalytic performances after a continuous 600-hour run. That is to say, their good activity and selectivity remained unchanged after a long time.

As can be seen from Table 1, the process for preparing the catalyst has a great influence on the catalytic performance of the catalyst. Specifically, the activity, selectivity and lifetime of a catalyst will vary depending upon the preparation process. The process for preparing the catalyst according to the present invention is effective. It is desired that the supported components and amounts thereof in the catalyst fall within the scope of the present invention. The property of the support used in the catalyst also has an influence in the catalytic performance of the catalyst. Preferably, the support according to the present invention was employed.

Example 11

The C5 cuts from a petroleum cracking unit, as shown in Table 2, was fed into the middle section of a light fraction removing column 1 with 75 plates. The light fractions having 4 or less carbon atoms and a portion of alkynes were obtained at the top of the column and the C5 materials were obtained at the bottom. The inlet temperature of C5 cuts was 65° C., the bottom temperature was 82° C., the top temperature was 50° C., the top pressure was 0.20 MPa, the bottom pressure was 0.24 MPa and the reflux ratio was 19.

The bottoms from the light fraction removing column 1 entered into a thermal dimerization reactor 2A where cyclopentadiene is dimerized to form dicyclopentadiene at a temperature of 80° C., a pressure of 1.2 MPa and a residence time of 65 min. The dimerized stream was fed into the middle section of a heavy fraction pre-removing rectification column 2B with 75 plates operating at the following conditions: a bottom temperature of 101° C., a top temperature of 52° C., a reflux ratio of 0.95, a top pressure of 0.06 MPa and a bottom pressure of 0.09 MPa. 1,3-pentadiene, dicyclopentadiene and other heavy fractions were obtained at the bottom, and isoprene, mono-olefins, alkanes, alkynes and cyclopentadiene were obtained at the top.

The stream out of the top of the heavy fraction pre-removing rectification column 2B was fed into a catalytic hydrogenation reactor 3 where a selective hydrogenation was carried out to remove alkynes. The reactor was packed with the hydrogenation catalyst obtained in Example 1, Cu—Ag—Pd—K/Al$_2$O$_3$. The reactor was operated at a temperature of 40° C., a pressure of 0.8 MPa and a liquid space velocity of 8 m³/m³·h.

The stream out of the hydrogenation reactor 3 was fed into the middle section of an extractive rectification column 4 with 114 plates where an extractive rectification was carried out in the presence of dimethylformamide as a solvent and sodium nitrite and ethanolamine as a composite polymerization inhibitor under the conditions of a top pressure of 0.19 MPa, a bottom pressure of 0.20 MPa, a bottom temperature of 138° C., a top temperature of 65° C., a overhead reflux ratio of 8.4 and a solvent ratio of 7.2. The concentration of sodium nitrite in C5 materials is 500 ppm and the concentration of ethanolamine in C5 materials is 300 ppm. Mono-olefins and alkanes were obtained at the top and the solvent-based materials rich in isoprene were obtained at the bottom.

The above solvent-based materials were fed into the middle section of a stripping column 5 operating under a condition of a plate number of 40, a top temperature of 44° C., a bottom temperature of 165° C., a top pressure of 0.12 MPa, a bottom pressure of 0.15 MPa and a reflux ratio of 3. The solvent obtained at the bottom was returned to the extractive rectification column 4 for recycling and the overhead stream was fed onto the 70$^{th}$ plate of a heavy fraction removing reaction rectification column 6.

The top temperature, bottom temperature, top pressure, bottom pressure, reflux ratio and plate number of the heavy fraction removing reaction rectification column 6 were 50° C., 62.5° C., 0.09 MPa, 0.10 MPa, 44.5 and 120 respectively. In the column, the unreacted cyclopentadiene was further reacted to form dicyclopentadiene, which was easy to be separated away. The isoprene of a polymerization grade was obtained at the top and isoprene, cyclopentadiene, dicyclopentadiene and other heavy fractions were drawn from the bottom.

The bottoms of the heavy fraction pre-removing rectification column 2B were fed into, at the 19$^{th}$ plate, the C5 removing column 7 operating under the following conditions together with the bottoms of the heavy fraction removing reaction rectification column 6: the top temperature, 47° C.; the bottom temperature, 105° C.; the top pressure, 0.02 MPa; the bottom pressure, 0.04 MPa; the plate number, 26; and the reflux ratio, 2.0. C5 hydrocarbons were obtained at the top of C5 removing column 7 and then fed into at the 43$^{rd}$ plate, a 1,3-pentadiene-refining column 8 operating under the following conditions: the plate number, 91; the top temperature, 52° C., the bottom temperature, 65° C., the top pressure, 0.05 MPa, the bottom pressure, 0.11 MPa and the reflux ratio, 40. 1,3-pentadiene product with a high purity was obtained at the bottom of the column 8. The overhead stream was returned to the line of C5 cuts. The bottoms of the C5-removing column 7 were fed into the middle section of a dicyclopentadiene refining column 9 operating under the following conditions: the plate number, 110; the top temperature, 37° C., the bottom temperature, 106° C., the column pressure, −0.08 MPa, and the reflux ratio, 2.5. The dicyclopentadiene product with a high purity was obtained at the bottom.

TABLE 2

Analysis of the stream in each unit %

| components | light fraction removing column 1 | | | thermal dimerization reactor 2A | | heavy fraction pre-removing rectification column 2B | | | hydrogenation reactor 3 | | extractive rectification 4 | |
|---|---|---|---|---|---|---|---|---|---|---|---|---|
| | feed | overheads | bottoms | feed | output | feed | overheads | bottoms | feed | output | feed | overheads |
| $C_4$ and $C_4^-$ | 4.60 | 28.41 | | | | | | 0.06 | | 0.06 0.06 | 0.06 | 0.09 |
| isopentane | 1.07 | 8.32 | 0.10 | 0.10 | 0.10 | | | 0.49 | | 0.49 0.49 | 0.49 | 0.34 |
| 3-methyl-1-butene | 4.64 | 27.42 | | | | | | 0.02 | | 0.02 0.22 | 0.22 | 0.77 |
| n-pentane | 1.74 | 0.07 | 2.10 | 2.10 | 2.13 | 2.13 | 3.19 | 1.53 | 3.19 3.19 | 3.19 | 8.27 |
| pentene-1 | 7.69 | 12.76 | 6.59 | 6.59 | 6.11 | 6.11 | 30.13 | 3.68 | 9.26 9.26 | 9.26 | 28.04 |
| 2-methyl-butene-1 | 4.49 | 2.55 | 4.80 | 4.80 | 4.87 | 4.87 | | | 7.37 8.17 | 8.17 | 20.15 |
| trans-2-pentene 1,4-pentadiene cis-2-pentene | 9.16 | 16.52 | 7.83 | 7.83 | 8.26 | 8.26 | | | 12.52 12.55 | 12.55 | 25.30 |
| 2-methyl-2-butene | 2.56 | 0.01 | 2.97 | 2.97 | 2.88 | 2.88 | 5.43 | 1.86 | 5.43 6.20 | 6.20 | 15.76 |
| cyclopentane | 0.98 | | 1.27 | 1.27 | 20.91 | 20.91 | | 3.81 | | | | 0.05 |
| isoprene | 16.70 | 0.57 | 19.29 | 19.29 | | | 53.31 | | 53.31 52.11 | 52.11 | 1.12 |
| cyclopentene | 4.29 | | 5.14 | 5.14 | 5.10 | 5.10 | 2.85 | 4.27 | 2.85 2.85 | 2.85 | 0.01 |
| butyne-2 | 0.31 | 2.16 | | | | | 0.02 | | 0.02 9 ppm | 9 ppm | |
| trans-1,3-pentadiene | 11.70 | 0.12 | 14.01 | 14.01 | 13.81 | 13.81 | 2.39 | 23.23 | 2.39 2.37 | 2.37 | 0.05 |
| cis-1,3-pentadiene | 5.99 | 0.07 | 7.14 | 7.14 | 7.14 | 7.14 | 0.23 | 14.03 | 0.23 0.22 | 0.22 | 0.01 |
| cyclopentadiene | 12.45 | 0.04 | 13.40 | 13.40 | 3.40 | 3.40 | 1.88 | 1.50 | 1.88 1.88 | 1.88 | 0.04 |
| valylene | | 0.47 | | | | | | | 0.08 10 ppm | 10 ppm | |
| $C_6$ | 5.89 | 0.51 | 5.36 | 5.36 | 5.94 | 5.94 | | 9.28 | | | |
| dicyclopentadiene | 4.80 | | 7.97 | 7.97 | 17.29 | 17.29 | | 33.77 | | | |
| $X_2'$ | 0.25 | | 0.37 | 0.37 | 0.32 | 0.32 | | 0.50 | | | |
| $X_1$ | 0.12 | | 0.18 | 0.18 | 0.20 | 0.20 | 0.31 | | 0.11 | 0.11 | |
| $X_2$ | 0.08 | | 0.11 | 0.11 | 0.15 | 0.15 | | 0.23 | | 0.21 | 0.21 |
| $X_3$ | 0.49 | | 0.70 | 0.70 | 1.39 | 1.39 | | 2.17 | | 0.11 | 0.11 |

| components | stripping column 5 | heavy fraction removing reaction rectification column 6 | | | C5-removing column 7 | | | 1,3-pentadiene-refining column 8 | | dicyclopentadiene-refining column 9 | |
|---|---|---|---|---|---|---|---|---|---|---|---|
| | overheads | feed | overheads | bottoms | feed | overheads | bottoms | overheads | bottoms | overheads | bottoms |
| $C_4$ and $C_4^-$ | | | | | | | | | | | |
| isopentane | | | | | | | | | | | |
| 3-methyl-1-butene | | | | | | | | | | | |
| n-pentane | | | | | 0.06 | 0.12 | | 0.92 | | | |
| pentene-1 | | | | | 0.02 | 0.03 | | 0.15 | 0.01 | | |
| 2-methyl-butene-1 | | | | | 0.04 | 0.09 | | 0.27 | 0.06 | | |
| trans-2-pentene 1,4-pentadiene cis-2-pentene | | | | | 0.15 | 0.30 | | 2.23 | 0.02 | | |
| 2-methyl-2-butene | | | | | 0.28 | 0.55 | | 3.72 | 0.10 | | |
| cyclopentane | | | | 0.03 | 2.17 | 3.28 | 1.06 | | 3.75 | 6.11 | |
| isoprene | 88.74 | 88.74 | 99.88 | 5.67 | 2.21 | 4.42 | | 34.46 | 0.13 | | |
| cyclopentene | 4.56 | 4.56 | 0.10 | 16.87 | 9.19 | 18.01 | 0.37 | 6.35 | 19.67 | 8.03 | 1.72 |
| butyne-2 | 20.2 ppm | 20.2 ppm | 24 ppm | | | | | | | | |
| trans-1,3-pentadiene | 3.11 | 3.11 | 0.005 | 30.5 | 22.52 | 42.80 | 2.24 | 37.42 | 43.57 | 11.96 | |
| cis-1,3-pentadiene | 0.21 | 0.21 | | 2.43 | 13.06 | 23.77 | 2.35 | 1.68 | 26.92 | 20.18 | |
| cyclopentadiene | 2.80 | 2.80 | <1 ppm | 8.04 | 2.38 | 2.34 | 2.42 | 12.37 | 0.91 | 10.99 | |
| valylene | 18 ppm | 18 ppm | 20 ppm | | | | | | | | |
| $C_6$ | | | | 10.80 | 2.55 | 19.05 | 1.04 | 2.77 | 38.80 | | |
| dicyclopentadiene | | | | 29.10 | 33.07 | 1.58 | 64.56 | 0.10 | 1.79 | 0.04 | 81.53 |
| $X_2'$ | | | | 0.02 | 0.72 | 0.03 | 1.41 | | 0.03 | 3.84 | 1.75 |
| $X_1$ | 0.18 | 0.18 | 0.01 | 1.23 | 0.52 | 0.09 | 0.95 | 0.29 | 0.06 | 0.05 | 2.81 |
| $X_2$ | 0.29 | 0.29 | | 3.74 | 0.32 | 0.08 | 0.56 | | 0.09 | | 2.44 |
| $X_3$ | 0.18 | 0.18 | | 2.37 | 2.57 | 0.11 | 5.03 | | 0.12 | | 9.75 |

Note:
$X_2'$ represents benzene and toluene;
$X_1$ represents dimers of C4-dienes and C5-dienes;
$X_2$ represents components consisting of homo-dimers of isoprene and 1,3-pentadiene;
$X_3$ represents components consisting of co-dimers of cyclopentadiene and isoprene, co-dimers of cyclopentadiene and 1,3-pentadiene, and a minor amount of homo-dimers of isoprene.

It can be seen from Table 2 that, the amounts of valylene and butyne-2 in the feed of the hydrogenation reactor 3 were respectively 0.08% and 0.02%. The amounts dropped to 9 ppm and 10 ppm respectively in the output stream after hydrogenation.

It can be seen that, the feed into the heavy fraction removing reaction rectification column 6 contained 2.80% of cyclopentadiene. The isoprene product of a polymerization grade with a purity of 99.88% was obtained at the top of the reaction rectification column, in which the content of cyclopentadiene was less than 1 ppm and the total alkyne content was less than 50 ppm. A 1,3-pentadiene product with a purity of 70.49% was obtained from the 1,3-pentadiene refining column 8. The dicyclopentadiene product with a purity of 81.53% was obtained from the dicyclopentadiene refining column.

Example 12

The C5 cuts from a petroleum cracking unit, as shown in Table 3, was fed into the middle section of a light fraction removing column 1 with a plate number of 75. The light fractions having 4 or less carbon atoms and a portion of alkynes were obtained at the top of the column and the C5 stream was obtained at the bottom. The inlet temperature of C5 cuts was 65° C., the bottom temperature was 82° C., the top temperature was 50° C., the top pressure was 0.20 MPa, the bottom pressure was 0.24 MPa and the reflux ratio was 19.

The bottoms from the light fraction removing column 1 entered into the middle section of a heavy fraction pre-removing reaction rectification column 2 with 95 plates and operating under the following conditions: a bottom temperature of 95° C., a top temperature of 52° C., a reflux ratio of 30, a top pressure of 0.10 MPa and a bottom pressure of 0.18 MPa. 1,3-pentadiene, dicyclopentadiene and other heavy fractions were obtained at the bottom, and isoprene, mono-olefins, alkanes, alkynes and cyclopentadiene were obtained at the top.

The stream out of the top of the heavy fraction pre-removing reaction rectification column 2 was fed into a catalytic hydrogenation reactor 3 where a selective hydrogenation was carried out to remove alkynes. The reactor was packed with the hydrogenation catalyst obtained in Example 1, Cu—Ag—Pd—K/Al$_2$O$_3$. The reactor was operated at a temperature of 40° C., a pressure of 0.8 MPa and a liquid space velocity of 8 m$^3$/m$^3$·h.

The stream out of the hydrogenation reactor 3 was fed into the middle section of an extractive rectification column 4 with 114 plates where an extractive rectification was carried out in the presence of dimethylformamide as a solvent and sodium nitrite and ethanolamine as a composite polymerization inhibitors under the conditions of a top pressure of 0.19 MPa, a bottom pressure of 0.20 MPa, a bottom temperature of 138° C., a top temperature of 65° C., a overhead reflux ratio of 8.4 and a solvent ratio of 7.2. The concentration of sodium nitrite in C5 materials is 500 ppm and the concentration of ethanolamine in C5 materials is 300 ppm. Mono-olefins and alkanes were obtained at the top and the solvent-based materials rich in isoprene were obtained at the bottom.

The above solvent-based materials were fed into the middle section of a stripping column 5 operating under a condition of a plate number of 40, a top temperature of 44° C., a bottom temperature of 165° C., a top pressure of 0.12 MPa, a bottom pressure of 0.15 MPa and a reflux ratio of 3. The solvent obtained at the bottom was returned to the extractive rectification column 4 for recycling and the overhead stream was fed onto the 70$^{th}$ plate of a heavy fraction removing reaction rectification column 6.

The top temperature, bottom temperature, top pressure, bottom pressure, reflux ratio and plate number of the heavy fraction removing reaction rectification column 6 were 50° C., 65° C., 0.09 MPa, 0.13 MPa, 44.5 and 120 respectively. In the column, the unreacted cyclopentadiene was further reacted to form dicyclopentadiene, which was easy to be separated away. The isoprene of a polymerization grade was obtained at the top, and isoprene, cyclopentadiene, dicyclopentadiene and other heavy fractions were withdrawn from the bottom.

The bottoms of the column 2 were fed into, at the 19$^{th}$ plate, the C5-removing column 7 operating under the following conditions together with the bottoms of the column 6: the plate number, 26; the top temperature, 47° C.; the bottom temperature, 105° C.; the top pressure, 0.02 MPa; the bottom pressure, 0.04 MPa; and the reflux ratio, 2.0. C5 hydrocarbons were obtained at the top of C5 removing column and then fed into, at the 43$^{rd}$ plate, a 1,3-pentadiene-refining column 8 operating under the following conditions: the plate number, 91; the top temperature, 52° C., the bottom temperature, 65° C., the top pressure, 0.05 MPa, the bottom pressure, 0.11 MPa and the reflux ratio, 40. A 1,3-pentadiene product with a high purity was obtained at the bottom of the column 8. The overhead stream was returned to the line of C5 cuts. The bottoms of the C5-removing column 7 were fed into the middle section of a dicyclopentadiene refining column 9 operating under the following conditions: the plate number, 110; the top temperature, 37° C., the bottom temperature, 106° C., the column pressure, −0.08 MPa, and the reflux ratio, 2.5. The dicyclopentadiene product with a high purity was obtained at the bottom.

TABLE 3

Analysis of the stream in each unit (%)

| components | light fraction removing column 1 | | | heavy fraction pre-removing reaction rectification column 2 | | | hydrogenation reactor 3 | | extractive rectification column 4 | |
| --- | --- | --- | --- | --- | --- | --- | --- | --- | --- | --- |
| | feed | overheads | bottoms | feed | overheads | bottoms | feed | output | feed | overheads |
| C$_4$ and C$_4^-$ | 4.60 | 28.41 | | | 0.06 | | 0.06 | 0.06 | 0.06 | 0.09 |
| isopentane | 1.07 | 8.32 | 0.10 | | 0.49 | | 0.49 | 0.49 | 0.49 | 0.34 |
| 3-methyl-1-butene | 4.64 | 27.42 | | | 0.02 | | 0.02 | 0.22 | 0.22 | 0.77 |
| n-pentane | 1.74 | 0.07 | 2.13 | 2.13 | 3.19 | 1.53 | 3.19 | 3.19 | 3.19 | 8.27 |
| pentene-1 | 7.69 | 12.76 | 6.11 | 6.11 | 30.13 | 3.68 | 9.26 | 9.26 | 9.26 | 28.04 |
| 2-methyl-butene-1 | 4.49 | 2.55 | 4.87 | 4.87 | | | 7.37 | 8.17 | 8.17 | 20.15 |
| trans-2-pentene | 9.16 | 16.52 | 8.26 | 8.26 | | | 12.52 | 12.55 | 12.55 | 25.30 |
| 1,4-pentadiene | | | | | | | | | | |
| cis-2-pentene | | | | | | | | | | |
| 2-methyl-2-butene | 2.56 | 0.01 | 2.88 | 2.88 | 5.43 | 1.86 | 5.43 | 6.20 | 6.20 | 15.76 |

TABLE 3-continued

Analysis of the stream in each unit (%)

| | | | | | | | | | | | |
|---|---|---|---|---|---|---|---|---|---|---|---|
| cyclopentane | 0.98 | | 20.91 | 20.91 | | 3.90 | | | | | 0.05 |
| isoprene | 16.70 | 0.57 | | | 53.31 | | 53.31 | 52.11 | 52.11 | | 1.12 |
| cyclopentene | 4.29 | | 5.10 | 5.10 | 2.85 | 4.27 | 2.85 | 2.85 | 2.85 | | 0.01 |
| butyne-2 | 0.31 | 2.16 | | | 0.02 | | 0.02 | 9 ppm | 9 ppm | | |
| trans-1,3-pentadiene | 11.70 | 0.12 | 13.81 | 13.81 | 2.39 | 23.53 | 2.39 | 2.37 | 2.37 | | 0.05 |
| cis-1,3-pentadiene | 5.99 | 0.07 | 7.14 | 7.14 | 0.23 | 14.03 | 0.23 | 0.22 | 0.22 | | 0.01 |
| cyclopentadiene | 12.45 | 0.04 | 13.40 | 3.40 | 1.88 | 1.50 | 1.88 | 1.88 | 1.88 | | 0.04 |
| valylene | | 0.47 | | | | | 0.08 | 10 ppm | 10 ppm | | |
| $C_6$ | 5.89 | 0.51 | 5.94 | 5.94 | | 9.28 | | | | | |
| dicyclopentadiene | 4.80 | | 17.29 | 17.29 | | 34.27 | | | | | |
| $X_2'$ | 0.25 | | 0.32 | 0.32 | | 0.50 | | | | | |
| $X_1$ | 0.12 | | 0.20 | 0.20 | | 0.25 | | 0.11 | 0.11 | | |
| $X_2$ | 0.17 | | 0.15 | 0.15 | | 0.17 | | 0.21 | 0.21 | | |
| $X_3$ | 0.40 | | 1.39 | 1.39 | | 1.40 | | 0.11 | 0.11 | | |

| | stripping column 5 | heavy fraction removing reaction rectification column 6 | | | C5-removing column 7 | | | 1,3-pentadiene-refining column 8 | | dicyclopentadiene-refining column 9 | |
|---|---|---|---|---|---|---|---|---|---|---|---|
| components | overheads | feed | overheads | bottoms | feed | overheads | bottoms | overheads | bottoms | overheads | bottoms |
| $C_4$ and $C_4^-$ | | | | | | | | | | | |
| isopentane | | | | | | | | | | | |
| 3-methyl-1-butene | | | | | | | | | | | |
| n-pentane | | | | | 0.06 | 0.12 | | 0.92 | | | |
| pentene-1 | | | | | 0.02 | 0.03 | | 0.15 | 0.01 | | |
| 2-methyl-butene-1 | | | | | 0.04 | 0.09 | | 0.27 | 0.06 | | |
| trans-2-pentene | | | | | 0.15 | 0.30 | | 2.23 | 0.02 | | |
| 1,4-pentadiene | | | | | | | | | | | |
| cis-2-pentene | | | | | | | | | | | |
| 2-methyl-2-butene | | | | | 0.28 | 0.55 | | 3.72 | 0.10 | | |
| cyclopentane | | | | 0.03 | 2.17 | 3.28 | 1.06 | | 3.75 | 6.11 | |
| isoprene | 88.74 | 88.74 | 99.88 | 5.67 | 2.21 | 4.42 | | 34.46 | 0.13 | | |
| cyclopentene | 4.56 | 4.56 | 0.10 | 16.87 | 9.19 | 18.01 | 0.37 | 6.35 | 19.67 | 8.03 | 1.72 |
| butyne-2 | 20.2 ppm | 20.2 ppm | 24 ppm | | | | | | | | |
| trans-1,3-pentadiene | 3.11 | 3.11 | 0.005 | 30.5 | 22.52 | 42.80 | 2.24 | 37.42 | 43.57 | 11.96 | |
| cis-1,3-pentadiene | 0.21 | 0.21 | | 2.43 | 13.06 | 23.77 | 2.35 | 1.68 | 26.92 | 20.18 | |
| cyclopentadiene | 2.80 | 2.80 | <1 ppm | 8.04 | 2.38 | 2.34 | 2.42 | 12.37 | 0.91 | 10.99 | |
| valylene | 18 ppm | 18 ppm | 20 ppm | | | | | | | | |
| $C_6$ | | | | | 10.80 | 2.55 | 19.05 | 1.04 | 2.77 | 38.80 | |
| dicyclopentadiene | | | | 29.10 | 34.07 | 1.58 | 66.18 | 0.10 | 1.79 | 0.04 | 85.86 |
| $X_2'$ | | | | 0.02 | 0.72 | 0.03 | 1.41 | | 0.03 | 3.84 | 1.75 |
| $X_1$ | 0.18 | 0.18 | 0.01 | 1.23 | 0.42 | 0.09 | 0.80 | 0.29 | 0.06 | 0.05 | 1.91 |
| $X_2$ | 0.29 | 0.29 | | 3.74 | 0.22 | 0.08 | 0.32 | | 0.09 | | 1.75 |
| $X_3$ | 0.18 | 0.18 | | 2.37 | 1.77 | 0.11 | 3.80 | | 0.12 | | 7.01 |

Note:
$X_2'$ represents benzene and toluene;
$X_1$ represents dimers of C4-dienes and C5-dienes;
$X_2$ represents components consisting of homo-dimers of isoprene and 1,3-pentadiene;
$X_3$ represents components consisting of co-dimers of cyclopentadiene and isoprene, co-dimers of cyclopentadiene and 1,3-pentadiene, and a minor amount of homo-dimers of isoprene.

It can be seen from Table 3 that, the amounts of valylene and butyne-2 in the feed of the hydrogenation reactor 3 were respectively 0.08% and 0.02%. The amounts dropped to 9 ppm and 10 ppm respectively in the output stream after hydrogenation.

It can be seen from the continued Table 3 that, the feed into the heavy fraction removing reaction rectification column 6 contained 2.80% of cyclopentadiene. The isoprene product of a polymerization grade with a purity of 99.88% was obtained at the top of the reaction rectification column, in which the content of cyclopentadiene was less than 1 ppm and the total alkyne content was less than 50 ppm. A 1,3-pentadiene product with a purity of 70.49% was obtained from the 1,3-pentadiene refining column 8. The dicyclopentadiene product with a purity of 85.86% was obtained from the dicyclopentadiene refining column.

It can be seen from the changes of parameters $X_1$, $X_2$ and $X_3$ as well as the purity of the dicyclopentadiene product in Tables 2–3 that, the purity of the dicyclopentadiene product can be further improved if the thermal dimerization and the heavy fraction pre-removing rectification are replaced by the reaction rectification.

What is claimed is:

1. A process for separating a C5 cuts obtained from a petroleum cracking process, comprising:
   1) a light fraction-removing step, wherein C5 cuts obtained from a petroleum cracking unit is fed into the middle section of a light fraction-removing rectification column 1 for rectification, with the light fractions having 4 or less carbon atoms being obtained at the top and C5 materials being obtained at the bottom;
   2) a heavy fraction pre-removing step, wherein the bottoms from step 1) are fed into a thermal dimerization reactor 2A where a thermal dimerization is carried out at a temperature of 60–150° C. and a pressure of 1.0–1.5 MPa, and cyclopentadiene in C5 cuts is dimerized to form dicyclopentadiene, and then the materials are fed into a heavy fraction pre-removing rectification column 2B, with dicyclopentadiene, 1,3-pentadiene and other heavy materials being obtained at the bottom, and isoprene, mono-olefins, alkanes, alkynes and cyclopentadiene being obtained at the top; or
   the bottoms from step 1) are fed into a heavy fraction pre-removing reaction rectification column 2 where a process of dimerization reaction and rectification separation is carried out, and cyclopentadiene in C5 cuts is dimerized to form dicyclopentadiene, with dicyclopentadiene, 1,3-pentadiene and other heavy materials being obtained at the bottom, and isoprene, mono-olefins, alkanes, alkynes, cyclopentadiene and 1,3-pentadiene being obtained at the top;

3) a catalytic hydrogenation step, wherein the overhead materials from step 2) are fed into a hydrogenation reactor 3 where a selective hydrogenation is carried out in the presence of a selective hydrogenation catalyst for alkynes in order to remove alkynes;

4) an extractive rectification step, wherein the materials from step 3) are fed into the middle section of an extractive rectification column 4 where an extractive rectification is carried out in the presence of a solvent and a polymerization inhibitor, with mono-olefins and alkanes being obtained at the top and the isoprene-rich and solvent-based materials of C5 dienes being obtained at the bottom;

5) a stripping step, wherein the solvent-based materials from 4) are fed into a stripping column 5; and 6) a heavy fraction-removing step, wherein the materials obtained at the top of the stripping column 5 are fed into a heavy fraction-removing reaction rectification column 6 for reaction rectification, and wherein the unreacted cyclopentadiene is dimerized to form dicyclopentadiene, with dicyclopentadiene, 1,3-pentadiene and other heavy materials being obtained at the bottom and isoprene of a polymerization grade being obtained at the top.

2. The process according to claim 1, wherein said heavy fraction pre-removing rectification column 2B is also a reaction rectification column, where the unreacted cyclopentadiene is further dimerized to form dicyclopentadiene, and the content of cyclopentadiene in the overhead materials is less than 2%, and wherein the plate number is 30–80, the bottom temperature is 50–110° C., the top temperature is 35–70° C., the reflux ratio is 0.5–35 and the operation pressure is 0.01–0.06 MPa.

3. The process according to claim 1, wherein the content of cyclopentadiene in the overhead materials of said heavy fraction pre-removing reaction rectification column 2 is less than 2%; the plate number is 50–120, the bottom temperature is 70–110° C., the top temperature is 35–70° C., the reflux ratio is 20–80 and the operation pressure is 0.01–0.20 MPa.

4. The process according to claim 1, wherein said catalytic hydrogenation reactor 3 is operated under a condition of a temperature of 20–80° C., a pressure of 0.3–4.0 MPa, a liquid space velocity of 2–15 m³/m³·h and a ratio of 1–30 mole hydrogen/mole alkyne.

5. The process according to claim 1, wherein said extractive rectification column 4 has a plate number of 70–150, an column pressure of 0.01–0.3 MPa, a bottom temperature of 100–150° C., a top temperature of 40–80° C., a reflux ratio of 4–15 and a solvent ratio of 3–12.

6. The process according to claim 1, wherein said stripping column 5 has a plate number of 20–60, a top temperature of 30–55° C., a bottom temperature of 120–200° C., a top pressure of 0.05–0.3 MPa, a bottom pressure of 0.08–0.5 MPa and a reflux ratio of 1–5.

7. The process according to claim 1, wherein the recovered solvent at the bottom of the stripping column 5 is returned to the extractive rectification column 4 for recycling.

8. The process according to claim 1, wherein said heavy fraction-removing reaction rectification column 6 has a plate number of 100–200, a top temperature of 40–55° C., a bottom temperature of 60–90° C., a top pressure of 0.01–0.15 MPa, a bottom pressure of 0.05–0.25 MPa and a reflux ratio of 15–60.

9. The process according to claim 1, wherein the bottoms from said heavy fraction pre-removing rectification column 2B or said heavy fraction pre-removing reaction rectification column 2 and the bottoms from the heavy fraction-removing reaction rectification column 6 are fed into a C5-removing column 7, and the overhead stream from said column 7 is fed into a 1,3-pentadiene refining column 8, and a 1,3-pentadiene product is obtained at the bottom and the overhead stream is returned to the C5-cut lines.

10. The process according to claim 9, wherein said bottoms from the C5-removing column are fed into a dicyclopentadiene refining column 9, at the bottom of which a dicyclopentadiene product is obtained.

11. The process according to claim 1, wherein the inlet temperature is 30–75° C., the bottom temperature is 75–96° C., the top temperature is 40–60° C., the top pressure is 0.1–0.3 MPa, the bottom pressure is 0.2–0.4 MPa, the plate number is 50–100 and the reflux ratio is 15–32, in the light fraction-removing column 1.

12. The process according to claim 9, wherein the top temperature is 40–55° C., the bottom temperature is 95–120° C., the top pressure is 0.01–0.03 MPa, the bottom pressure is 0.02–0.07 MPa, the plate number is 15–50 and the reflux ratio is 0.5–3, in the C5-removing column 7.

13. The process according to claim 9, wherein the top temperature is 40–60° C., the bottom temperature is 50–70° C., the top pressure is 0.02–0.1 MPa, the bottom pressure is 0.07–0.15 MPa, the plate number is 70–120 and the reflux ratio is 30–70, in the 1,3-pentadiene refining column 8.

14. The process according to claim 10, wherein the top temperature is 20–50° C., the bottom temperature is 90–120° C., the column pressure is from −0.05 to −0.12 MPa, the plate number is 70–160 and the reflux ratio is 1–5, in the dicyclopentadiene refining column 9.

15. The process according to claim 1, wherein said solvent is selected from the group consisting of dimethylformamide, dimethylacetamide, acetonitrile, N-methyl pyrrolidone and the mixtures thereof.

16. The process according to claim 1, wherein said selective hydrogenation catalyst for alkynes comprises, based on the total weight of the catalyst, more than 50% of aluminum oxide support, and (1) at least one metal selected from the IB group of the Elemental Periodic Table at an amount of 0.1–10%;

(2) at least one metal selected from the VIII group of the Elemental Periodic Table at an amount of 0.008–1%;

(3) at least one alkali metal at an amount of 0.01–5%.

17. The process according to claim 1, wherein said selective hydrogenation catalyst for alkynes is prepared by: firstly, impregnating the support with a nitric acid solution of a salt of IB group metal, secondly with a nitric acid solution of a salt of VIII group metal, and then with an aqueous solution of an alkali metal compound; drying the impregnated support at a temperature of 50–200° C. to remove water after each step of impregnation; and optionally calcining the dried support at a temperature of 250–650° C.

18. The process according to claim 16, wherein said metal from the IB group employed in said selective hydrogenation catalyst is at least one of copper and silver, and wherein the amount of copper is at least 90% based on the total weight of metals of IB group; said metal from the VIII group is palladium; and said alkali metal is potassium.

19. The process according to claim 16, wherein the amount of said support is more than 90% by weight.

20. The process according to claim 17, wherein the pH of said nitric acid solution of a salt of IB group metal and that of a salt of VIII group metal are in the range of 0.1–3.

21. The process according to claim 20, wherein the pH of said nitric acid solution of a salt of IB group metal and that of a salt of VIII group metal are in the range of 0.2–2.

22. The process according to claim 17, wherein said salt of IB group metal and said salt of VIII group metal are nitrate.

23. The process according to claim 17, wherein said alkali metal compound is hydroxide.

24. The process according to claim 16, wherein the amounts of the supported components are as follows: IB group metal, 1%–8%; VIII group metal, 0.01%–0.2%; and alkali metal, 0.1%–2%.

25. The process according to claim 16, wherein the amounts of the supported components are as follows: IB group metal, 2%–6%; VIII group metal, 0.01%–0.1%; and alkali metal, 0.2%–1%.

26. The process according to claim 16, wherein the specific surface area of said support is 200–350 $m^2/g$.

27. The process according to claim 26, wherein the pore volume of said support is 0.1–1.0 ml/g and the average pore size of said support is 4–40 nm.

28. The process according to claim 17, wherein said support is calcined at a temperature of 300–800° C. for 2–10 hours prior to impregnation.

29. The process according to claim 1, wherein the polymerization inhibitor is selected from the group consisting of sodium nitrite and ethanolamine composite, o-nitrophenol, nitrobenzene and furfural.

30. The process according to claim 29, wherein the polymerization inhibitor is sodium nitrite and ethanolamine composite, and the concentration of sodium nitrite in C5 materials is 200–1500 ppm and the concentration of ethanolamine in C5 materials is 100–700 ppm.

* * * * *